US012765859B2

(12) United States Patent
King et al.

(10) Patent No.: US 12,765,859 B2
(45) **Date of Patent: *Oct. 20, 2026**

(54) SYSTEM FOR DETERMINING PERIPHERAL ARTERY DISEASE AND METHOD OF USE

(71) Applicant: BLUEDOP MEDICAL, LTD., Nottingham (GB)

(72) Inventors: David King, London (GB); Michael Graeme Taylor, London (GB); Patrick Kelly, Sioux Falls, SD (US); Mohammed Al-Qaisi, Nottingham (GB)

(73) Assignee: BlueDop Medical, Ltd., Nottingham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 19/030,973

(22) Filed: Jan. 17, 2025

(65) Prior Publication Data

US 2025/0160783 A1 May 22, 2025

Related U.S. Application Data

(63) Continuation of application No. 18/202,199, filed on May 25, 2023, now Pat. No. 12,245,885, which is a continuation of application No. 15/353,862, filed on Nov. 17, 2016, now Pat. No. 11,660,063.

(60) Provisional application No. 62/257,191, filed on Nov. 18, 2015.

(51) Int. Cl.
*A61B 8/00* (2006.01)
*A61B 8/04* (2006.01)
*A61B 8/06* (2006.01)
*A61B 8/08* (2006.01)

(52) U.S. Cl.
CPC .................. *A61B 8/06* (2013.01); *A61B 8/04* (2013.01); *A61B 8/0891* (2013.01); *A61B 8/461* (2013.01); *A61B 8/488* (2013.01); *A61B 8/5223* (2013.01)

(58) Field of Classification Search
CPC ..... A61B 5/02007; A61B 5/021; A61B 5/022; A61B 5/026; A61B 5/0263; A61B 8/06; A61B 8/4245; G01R 33/56308
See application file for complete search history.

(56) References Cited

U.S. PATENT DOCUMENTS

| | | | | |
|---|---|---|---|---|
| 5,409,010 A * | 4/1995 | Beach | G01S 7/52071 | 600/455 |
| 2010/0234731 A1* | 9/2010 | Lu | G01S 7/52066 | 600/454 |

(Continued)

*Primary Examiner* — Christopher L Cook
(74) *Attorney, Agent, or Firm* — Craig Fieschko; DeWitt LLP

(57) ABSTRACT

A system for determining peripheral artery disease and method of use for determining the presence or absence of peripheral vascular disease and the severity of the disease in particular vascular segments. The System for determining peripheral artery disease and method of use includes a continuous wave Doppler transceiver which generates a digitized version of quadrature detected stereo audio and is coupleable to a waveform converter and processor. The waveform converter and processor provides filtering, time domain to frequency domain conversion, gain control, and statistical processing of the converted Doppler Stereo audio and is operationally coupled to a display for presenting results to a technician.

9 Claims, 4 Drawing Sheets

(56) References Cited

U.S. PATENT DOCUMENTS

| | | | | |
|---|---|---|---|---|
| 2013/0281862 | A1* | 10/2013 | Yoon | A61B 8/5223 600/454 |
| 2014/0358000 | A1* | 12/2014 | Gupta | A61B 8/469 600/455 |

* cited by examiner

SYSTEM FOR DETERMINING PERIPHERAL ARTERY DISEASE AND METHOD OF USE

REFERENCE TO PRIOR APPLICATIONS

This application is a Continuation of U.S. patent application Ser. No. 18/202,199, filed May 25, 2023; which is a Continuation of U.S. patent application Ser. No. 15/353,862, filed Nov. 17, 2016 (issued May 30, 2023 as U.S. Pat. No. 11,660,063); which claims priority from U.S. Provisional Application No. 62/257,191, filed Nov. 18, 2015, each of which is hereby incorporated by reference in its entirety.

FIELD OF THE INVENTION

The present invention relates to methods for determining peripheral vascular disease and obtaining haemodynamic data and more particularly pertains to a new system for determining the presence or absence of peripheral vascular disease and the severity of the disease in particular vascular segments.

BACKGROUND ART

Haemodynamics (or Hemodynamics) is the fluid dynamics of blood flow. The circulatory system is controlled by homeostatic mechanisms, much as hydraulic circuits are controlled by control systems. Haemodynamic response continuously monitors and adjusts to conditions in the body and its environment. Thus, haemodynamics explains the physical laws that govern the flow of blood in the blood vessels. The relationships can be challenging because blood vessels are complex, with many ways for blood to enter and exit under changing conditions.

The heart is the driver of the circulatory system, pumping blood through rhythmic contraction and relaxation. The rate of blood flow out of the heart (often expressed in L/min) is known as the cardiac output (CO).

Blood being pumped out of the heart first enters the aorta, the largest artery of the body. It then proceeds to divide into smaller and smaller arteries, then into arterioles, and eventually capillaries, where oxygen transfer occurs. The capillaries connect to venules, and the blood then travels back through the network of veins to the right heart. The microcirculation—the arterioles, capillaries, and venules—constitutes most of the area of the vascular system and is the site of the transfer of $O_2$, glucose, and enzyme substrates into the cells. The venous system returns the de-oxygenated blood to the right heart where it is pumped into the lungs to become oxygenated and $CO_2$ and other gaseous wastes exchanged and expelled during breathing. Blood then returns to the left side of the heart where it begins the process again.

In a normal circulatory system, the volume of blood returning to the heart each minute is approximately equal to the volume that is pumped out each minute (the cardiac output). Because of this, the velocity of blood flow across each level of the circulatory system is primarily determined by the total cross-sectional area of that level. This is mathematically expressed by the following equation:

$$v = Q/A$$

where v=velocity (cm/s)

Q=blood flow (ml/s)

A=cross sectional area ($cm^2$)

The blood pressure in the circulation is principally due to the pumping action of the heart. The pumping action of the heart generates pulsatile blood flow, which is conducted into the arteries, across the micro-circulation and eventually, back via the venous system to the heart. During each heartbeat, systemic arterial blood pressure varies between a maximum (systolic) and a minimum (diastolic) pressure. In physiology these are often simplified into one value, the mean arterial pressure (MAP), which is calculated as follows:

$$MAP \approx 2/3(BP_{dia}) + 1/3(BP_{sys})$$

Note: $BP_{dia}$ weighted more heavily since the heart spends two thirds of the heart beat cycle in the diastolic.

where:

MAP=Mean Arterial Pressure $BP_{dia}$=Diastolic blood pressure $BP_{sys}$=Systolic blood pressure A stenosis is an abnormal narrowing of a blood vessel. A stenosis may be caused by atherosclerosis, diabetes, ischemia, calcification, infection, birth defects, or smoking. An occlusion is a blockage of a blood vessel. Either a stenosis or an occlusion affects the ability of a blood vessel to allow blood flow and may restrict or block blood flow.

With human life expectancy increasing worldwide the effects of progressive arterial disease become more apparent within the ageing population. This disease commonly takes the form of stenosis (localized cross sectional arterial narrowing) which may represent a significant resistance to blood flow in, for instance, the iliac, femoral, popliteal, peroneal, tibial, and pedal arteries resulting in claudication or critical limb ischemia. The effect of a stenosis on resistance is nonlinear, causing symptoms when narrowing exceeds a threshold value.

Where narrowing completely obscures the arterial cross section the stenosis becomes an occlusion. In this case smaller calibre arteries (collateral) direct blood flow past the occlusion, often rejoining the original arterial pathway downstream of the occlusion. In effect the collateral pathway can be modelled as a special case of a stenosis. It should be noted that collateral flow also starts to develop around a stenosis as the lumen becomes more obscured. In what follows a stenosis or an occlusion will be used interchangeably where permitted by the context and will be referred to collectively as 'disease' or 'a lesion'.

In order to gauge the clinical significance of individual lesions, local haemodynamic information needs to be obtained.

Ultrasound based Doppler shift spectral analysis and imaging techniques using Continuous Wave Doppler and Duplex scanning machines allow velocity and (in the latter case) flow rate data to be directly measured non-invasively in many accessible parts of the vascular network. Similarly, techniques exist for calculating blood velocity and flow rates from Magnetic Resonant Imaging (MRI) data (see 'Real-time volumetric flow measurements with complex-difference MRI' Thompson R B and Mcveigh E R in Magnetic Resonance in Medicine Vol 50, Issue 6, Pages 1248-1255, herewith incorporated by reference herein). MRI data can be obtained from all parts of the vascular network, some of which are inaccessible to ultrasound scanners.

The use of both invasive and non-invasive techniques to determine the existence and extend of peripheral vascular disease (peripheral arterial disease; progressive arterial disease, PAD, artheriosclerosis obliterans, and similar conditions (collectively referred to herein as PAD) is known in the prior art. Additionally, techniques for measuring local mean blood pressure from velocity or flow rate waveforms and their application to detecting stenosis is also known. As an illustrative example refer to United States Patent Application publication US 2012/0123246 A1 published on May 17, 2012 to King et. al. which is hereby incorporated by reference.

PAD may first show its effects in the legs and feet. The narrowing of the arteries may progress to total closure (occlusion) of the vessel. The vessel walls become less elastic and cannot dilate fully or at all to allow greater blood flow when needed, such as during exercise. This is a common disorder, which can affect anyone, but often affects men over 50 years old. PAD is one of the fastest growing disease processes in the world and may affect over 200 million people worldwide. PAD has been estimated to affect 12% to 14% of the general population. The majority of patients are asymptomatic (do not show symptoms) and are undiagnosed. For patients with symptoms, the symptoms often affect one limb and may present as leg pain (intermittent claudication) which may be aggravated by exercise and relieved with rest; numbness of the legs or feet at rest; cold legs or feet, muscle pain in the thighs, calves, or feet; change of color of the legs; paleness or blueness (cyanosis), a weak or absent pulse in the limb, or walking/gait abnormalities. However, it has been estimated that approximately one-third of patients with symptoms of PAD do not report them to their doctor. As a result of both asymptomatic and unreported cases, a high risk group of patients are under diagnosed and receive either no treatment or sub-optimal treatment.

There are several currently utilized modalities used for diagnosing PAD. PAD may be revealed by an abnormal ratio between the blood pressure of the ankle and arm (ankle/brachial index or ABI). A decrease in blood pressure from the brachial artery (close to the bicep in the upper arm) to the ankle would suggest a stenosis (narrowing) or an occlusion (blockage) in the arteries somewhere between the Aorta and the ankle.

The test for determining ABI may be performed with a sphygmomanometer (blood pressure cuff and gauge) and a stethoscope or continuous wave Doppler ultrasonic probe for detecting the sound waves associated with the blood flow. The systolic pressure may be determined for each location and compared in the form of a ratio. This test may be performed in a physician's office, laboratory, or even in the field. However, the medical personnel performing this test must have a basic knowledge of arterial anatomy and must be trained in how to perform the ABI testing such that valid and repeatable reading may be obtained. Thus, while it is not necessary to have a physician perform the test, skilled personnel are generally required.

Historically, ankle/brachial pressure index (ABPI) has been used as a convenient indicator of clinically significant peripheral arterial disease in the lower limbs. Systolic pressure can be simply obtained by placing a CW Doppler device over the artery immediately downstream of an encompassing pressure cuff. When the cuff is inflated to equal or just exceeds the systolic blood pressure within the artery, the audio signal from the Doppler device will cease. By recording the cuff pressure at that precise moment, the intra-arterial systolic pressure is assumed to be equal the cuff pressure. An arm and an ankle blood pressure cuff are applied. In the presence of one or more clinically significant lesions within the arteries supplying the lower limbs, the ratio between ankle/arm systolic pressures falls below a pre-established threshold value. This measurement is typically carried out on a rested, supine subject.

While ABI is currently used to diagnose PAD, it is not accurate in calcified diabetic lesions (stenosis or occlusions), which may make up more that 30% of all PAD patients. It does not work because calcified lesions are incompressible causing an artificially high pressure reading in the ankle and a falsely elevated ABI. Additionally, it is challenging to perform properly in chair bound patients, and is often too painful for patients with foot or ankle wounds. The cuff may be painful or introduce infection to their wounds.

In some instances, ABI is used with duplex and/or Doppler waveforms to try to overcome these limitations. However, in such cases, generally vascular surgeons and/or radiologists are required to interpret the results, which significantly increases the cost, and limits the availability of meaningful detection.

Distally the circulatory system consists of a series of arterial bifurcations. The characteristic resting blood flow waveforms in the major transit blood vessels are dominated by constructive interference between flow waves reflected from the periphery and re-reflected from the bifurcation. This results in a distinctive notch (a change in slope direction from negative to positive that occurs during diastole after the dicrotic notch) in the flow waveform shape within disease free arterial system, referred to herein as a 'C-notch'. In the presence of proximal disease the constructive interference changes to destructive interference, effectively eliminating the C-notch.

In these respects, the system for determining peripheral artery disease and method of use according to the present invention substantially departs from the conventional concepts and designs of the prior art, and in so doing provides an apparatus primarily developed for the purpose of providing a clear indication of the presence or absence of PAD and significantly reducing the amount of training necessary to reliably and repeatedly perform the diagnostic test.

SUMMARY OF THE INVENTION

In view of the foregoing disadvantages inherent in the known types of haemodynamic measurement and monitoring systems and methods now present in the prior art, the present invention provides a new System For Determining Peripheral Artery Disease and Method of Use wherein the same can be utilized for analyzing a Doppler waveform providing a clear indication of the presence or absence of PAD and significantly reducing the amount of training necessary to perform the diagnostic test in a repeatable and reliable manner.

To attain this, the present invention generally comprises a Doppler transceiver, a waveform converter and processor, and a display from providing a visual result for the user.

Various embodiments and implementations of the present invention will be provided. It is important to note that a limitation described in one embodiment or implementation is not necessarily a limitation for any other embodiment or implementation unless specifically described as such.

In an embodiment, the person performing the testing using the present invention (referred to as a "technician" without regard to the degree of skill or training of any particular user) will use the continuous wave Doppler transceiver to obtain stereo audio of the blood flow through the vessels of concern, such as a femoral, popliteal, peroneal, anterior tibial, posterior tibial or pedal artery. It is important to note, that while the present invention has significant applicability as a replacement for a traditional ABI test, it also has broader applicability for testing other arterial structures and fistuals. Also, it is important to note that the technician obtains the stereo audio of the blood flow in the vascular segment of interest without the need of a pressure cuff allowing for greater applicability including patients in a seated position, those with open wounds, and those with significant calcification which may result in limited compressibility or incompressibility of the blood vessel of interest.

In a further embodiment, the continuous wave Doppler transceiver is wireless. In such an embodiment, the continuous wave Doppler transceiver transmits the audio information to the waveform converter and processor. Those skilled in the art will recognize that the format of the audio information may take on many forms without departing from the spirit of the present invention. It is preferred however that the audio information is digitized at this stage to improve transmission characteristics and performance, and to reduce the likelihood of interference during transmission.

In a further preferred embodiment, the Doppler stereo audio produced by the wireless Doppler transceiver is the baseband converted version of the Doppler-shift signals received back from moving blood. This is produced within the wireless Doppler transceiver by quadrature detection, allowing for the directionality of movement to be preserved (towards versus away from the transducer).

In still a further embodiment, the waveform converter and processor receives a digitized version of the stereo audio of the blood flow and processes the signal to reduce artifacts.

The waveform converter and processor is a physical device which provides filtering, time domain to frequency domain conversion, gain control, and statistical processing of the converted Doppler Stereo audio. This may be implemented as an all hardware solution, or as a hardware device which implements specific functions through software controlled processors. It should also be understood that for at least the purposes of this illustrative embodiment, that the waveform converter and processor is operationally coupled to a "real time" visual display of the Doppler Stereo Audio and audio itself is provided to aid the operator in finding the appropriate blood vessel and maximizing the signal received.

In at least one embodiment, the processing typically includes, but may not be limited to:

(a) taking a short time series of audio samples;
(b) weighting the data to limit "end effects" of sampling;
(c) performing a Complex Fast Fourier Transform;
(d) taking the moduli of the frequency values; and
(e) unscrambling the amplitude values to represent forward and reverse signal.

The system described broadly herein aids the operator in identifying the presence of a C-notch that they would not be able to identify in an accurate and repeatable manner without the use of the described invention. It aids the operator in several ways including eliminating variability in the analyzed data that results from operator or patient movement, only accepting data that is representative of physiologically accurate waveforms, ignoring data where a dicrotic notch is present, and identifying significant disease by identifying a lack of features in the waveform that result from summing reflected waves in healthy patients.

There has thus been outlined, rather broadly, several important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

The invention will be better understood and objects of the invention will become apparent when consideration is given to the following detailed description thereof. Such description makes reference to the annexed drawings wherein.

DETAILED DESCRIPTION

Figure 1:
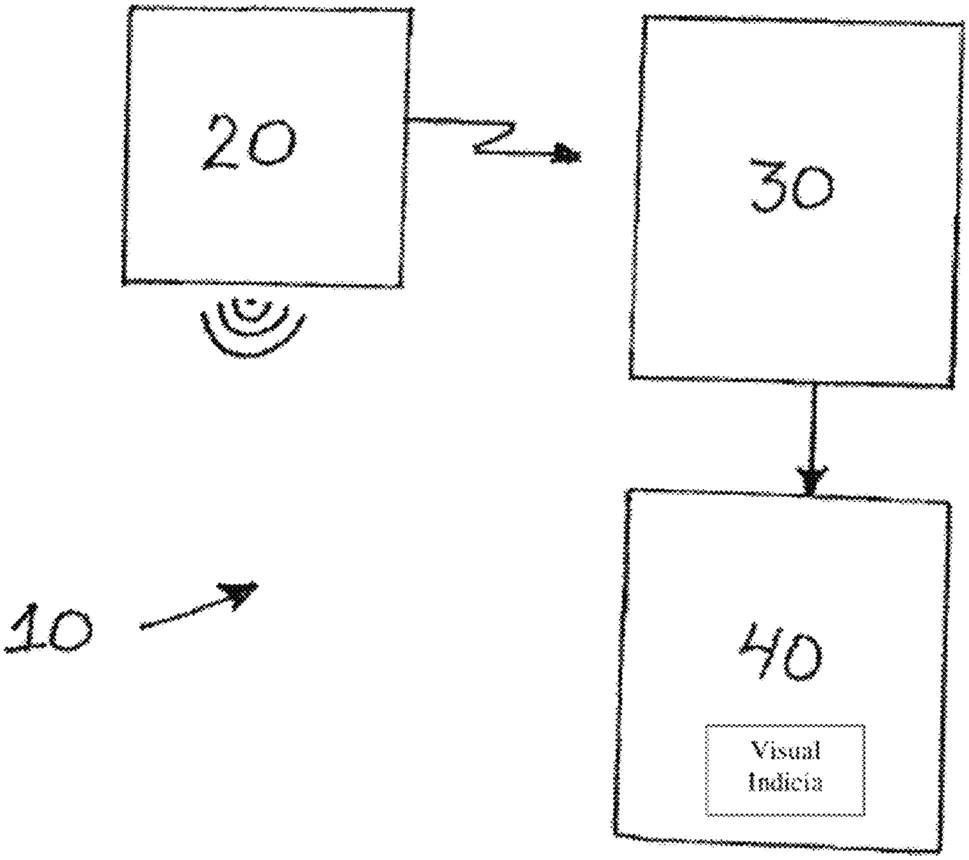
FIG. 1 is a schematic functional block diagram representation of an embodiment of the present invention.

With reference now to the drawings, and in particular to FIGS. 1 through 4 thereof, a new System For Determining Peripheral Artery Disease and Method of Use embodying the principles and concepts of the present invention and generally designated by the reference numeral 10 will be described.

With the preceding general description of the system of the present invention as background, we now address the specific advantages of the present invention in being able to present not only an improved solution for providing a clear indication of the presence or absence of PAD to the technician and other diagnostic improvements as discussed below.

The present invention is able to detect a 'C-notch' in the converted Doppler stereo audio which is indicative of the presence or absence of PAD.

As described above the present invention 10 incorporates a waveform converter and processor 20, which in part converts the Doppler stereo audio into a frequency domain (velocity flow) representation which can be presented to the technician through the display. Traditional Doppler waveform analysis when compared to invasive angiography has provided insights into "normal" waveforms as well as changes in these waveforms caused by various degrees of stenosis or occlusion. A discussion of these waveforms in included in Monotonic Doppler Ultrasound Spectral Waveforms in Peripheral Arterial Disease by Dr. M. Al-Qaisi, Thesis for the Degree of Doctor of Medicine (M.D.), University of London, 2010 ("Al-Qaisi Thesis"), which is hereby incorporated by reference.

The Al-Qaisi Thesis also includes a detailed discussion of the potential applicability of Monotonic waveforms, specifically their presence or absence, as a detection of significant arterial disease. A monotonic waveform is defined as one that does not include the C-notch. A non-monotonic waveform does include the C-notch. The present invention build on this foundation and provides significant improvement by providing a statistical analysis of Doppler waveforms to provide a standalone indication of presence or absence of significant disease without requiring highly skilled individuals to provide an interpretation of the Doppler waveforms.

Figure 2:
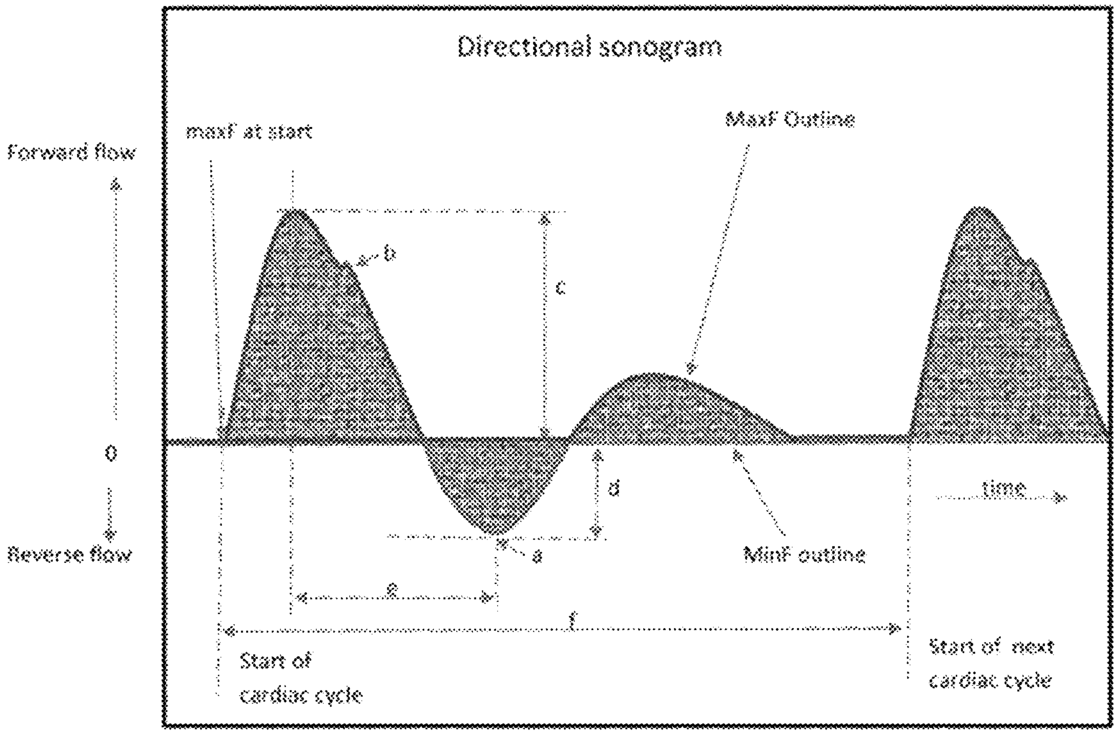
FIG. 2 is a schematic diagram of an illustrative waveform with a C-Notch of a nominal healthy patient.

FIG. 2 shows various aspects of a waveform which includes the C-notch including; (a)—designation of the C-notch; (b)—the waveform; (c) the systolic peak; (d) the negative peak, (e) the time from the systolic peak to the secondary peak, and (f) the time of a single cardiac cycle.

Figure 3:
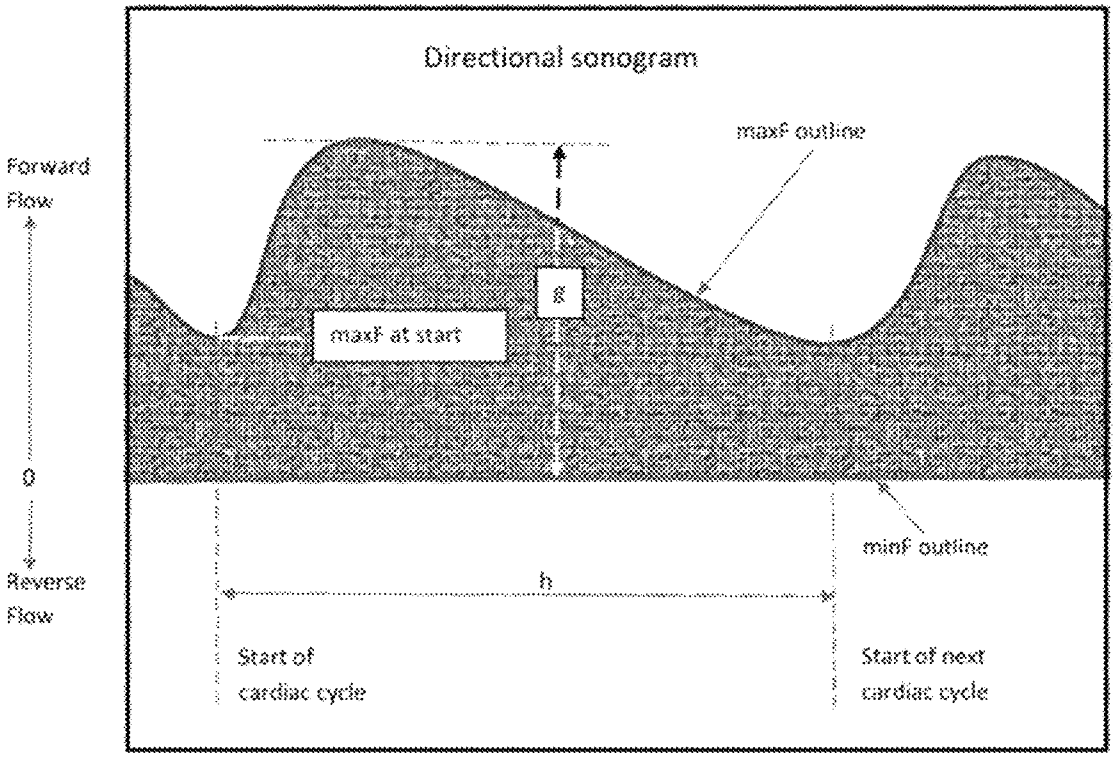
FIG. 3 is a schematic diagram of an illustrative waveform indicating serious disease.
Figure 4:
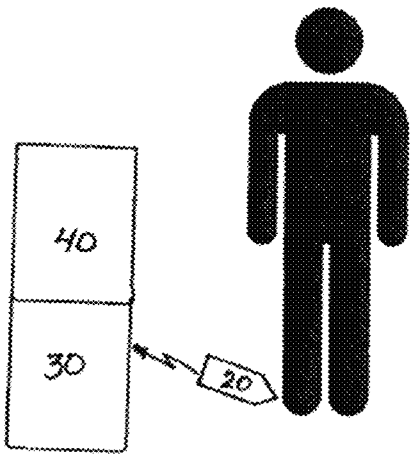
FIG. 4 is a schematic diagram of an embodiment of the present invention in use.

FIG. 3 shows the (g)—systolic peak and (h) the time of a single cardiac cycle for a waveform which does not include the notch for a patient having significant disease.

In at least one preferred embodiment, the Doppler transceiver 20 is uniquely paired with the waveform converter and processor 30 to limit interference from other units and to enhance data security.

The basic functionality of the waveform converter and processor 30 shall be described in the next several paragraphs. While the waveform converter and processor 30 may be implemented in an all hardware configuration or in a hardware configuration which utilizes software controlled processors, the following description may include terms of art typical of software implementations for purposes of clarity, but such terminology should not be read as requiring a software implementation.

The waveform converter and processor 30 receives the Doppler stereo audio data from the Doppler transceiver 20 and then spectrally analyzes the signal to produce a directional sonogram (which may be displayed), determine the maximum frequency outline in both directions, and finally generate from these outlines various numerical parameters and clinical indicators.

In at least one preferred embodiment, the waveform converter and processor 30 performs functions including:

- Taking a short time series of audio samples (128×2 data values);
- Weighting the data to limit 'end effects' of sampling (Hanning Weighting);
- Performing a Complex Fast Fourier Transform (128*2 frequency values);
- Taking the moduli of the frequency values (128 amplitude values);
- Unscrambling the amplitude values to represent forward and reverse signal. AF0-AF63 unchanged, AF64-AF127 become AF-64-AF-1; and
- Setting amplitude AF0 to zero.

Dependent of the data sampling rate, a form of 'sliding transform' is implemented in order to maintain a standard sonogram display with a time display resolution of 10 ms. Display frequency ranges of +/−8 kHz, +/−4 kHz or +/−2.5 kHz are provided to cover the range of signals found clinically.

The sliding transform process allows a full 128 data point FFT to be performed every 10 ms, whether or not 128 new data samples have actually been created within this time period. An appropriate number of old samples maybe used along with the newly available samples to make up the total of 128.

| RANGE | SAMPLE RATE | SAMPLES/10 mS | REUSED |
|---|---|---|---|
| +/−8 kHz | 16 ksps | 160 | 0 |
| +/−4 kHz | 8 ksps | 80 | 48 |
| +/−2.5 kHz | 8 ksps | 50 | 78 |

This process results in a common data output rate independent of display frequency range, and gives a practical time and frequency resolution of ~1% for clinical blood flow signals.

Since the 1970s, the maximum frequency outline of the Doppler spectral display has been used as the most significant feature of the sonogram, and shown to be clinically indicative of health and disease.

The present invention determines the outline, based on the full data within each vertical spectral line and also that of nearby lines. Forward and reverse data are treated separately.

For each direction of flow, the amplitudes are accumulated through the whole frequency range from F1 to F63, (ignoring any amplitude below a small threshold). The total is divided by 16, and then a subtraction process is performed on the total/16, from F63 down to F1, stopping when the accumulator reaches zero. This gives a '15/16 MaxF'. The result is then scaled back up by multiplying the result by 16/15.

As most Doppler flow signals have the form of 'bounded white noise' with some additional background noise, this has been found to produce a good equivalent to manual waveform outlining.

Further processing smooths the outline in time—to limit the short term outline variations, given that the underlying audio signal is stochastic in nature.

In a further embodiment, median filtering is used to reduce the effect of sudden drops/spikes in individual spectral sweeps. The MaxF for a given point in time is replaced by the median value of the MaxF from t−2 to t+2 (a 5 point median).

In still a further embodiment, this is then further smoothed by using a simple 5 point smoothing algorithm on the median'd data, each MaxF being the average of its adjacent points (t−2 to t+2).

While this can smooth out sharp dips/bumps in the MaxF outline, it provides a more statistically reliable value and minimizes drop-outs and spikes caused when the gain is low or that are caused by operator hand or patient movement.

Preferably, the waveform converter and processor 30 superimposes the MaxF and MinF outlines on the sonogram in real-time to assist the operator in setting the appropriate gain and identifying any interfering signals.

Deriving Parameters and Features From the Sonogram Outlines

At the end of each four second sonogram sweep, the updating of the sonogram pauses and the MaxF/MinF data is interrogated. If the data is determined as satisfactory, the derived values are presented on the display 40. Otherwise, further sonogram data is gathered until such time as valid data is detected.

In at least one embodiment, an option to average the spectral data may be used if the individual 4 second sonograms fail to provide valid data promptly. This takes four screens worth of sonogram and superimposes the data from all recognized cardiac cycles to produce one 'ensemble average' cycle. This average is then displayed and reanalyzed. This rarely fails to obtain a result.

Identifying Individual Cardiac Cycles

As the systolic upswing in the Doppler flow data is the single most significant and reliable indicator of the cardiac cycle, the process of identifying these is performed by identifying the maximum height of the MaxF outline across the whole 4 seconds of data (bigpeak).

The gradient of the forward MaxF waveform across the 4 seconds is determined, and then each local minimum is found together with its first following maximum. This produces a table of peaks being possible cardiac cycle starts.

If at least two 'peaks' are found, the data is checked and accepted as 'possible' systolic peaks if each identified 'peak' is at least 75% of the 'bigpeak' and the difference in height from foot to peak is greater than $3/64$.

Finally, short cardiac cycles are rejected if peak-peak time is less than 400 ms (40 sweeps). A resultant table of 'goodpulses' results, containing both heights and positions of each accepted cardiac cycle start (foot), systolic peak and any further small positive peaks.

Monotonicity Detection

The present inventions uses monotonicity detection as an indication of arterial disease. Monotonicity is defined here as: the absence of any peak in MaxF outline between the forward systolic peak and end diastole (the foot of the following waveform) when forward flow exists, throughout the cardiac cycle (height of next foot>0), and no reverse flow peaks exist.

The first requirement is to detect any post-systolic upswing, which is done by searching across the cardiac cycle data already tabulated, from systolic peak to next foot, noting the first detected upswing which has a rise of greater than $1/20$ the size of the cycle's own systolic foot-to-peak amplitude, whilst not reaching a maximum value greater than 70% of its associated systolic peak.

This has been found to avoid false detection due to remaining stochastic variations in MaxF and due to drop-out or mis-identification of systolic peaks.

The position of each foot, systolic peak and second positive peak (if present) are superimposed as vertical lines on the frozen sonogram.

Before conclusive decisions are made, the reverse flow MinF data is processed to identify any negative flow peaks.

All negative peaks which rise from zero to a maximum greater than $2/64$ are identified in the MinF data.

For each direction of flow, the amplitudes are accumulated through the whole frequency range from F1 to F63, (ignoring any amplitude below a small threshold). The total is divided by 16, and then a subtraction process is performed on the total/16, from F63 down to F1, stopping when the accumulator reaches zero. This gives a '$15/16$ MaxF'. The result is then scaled back up by multiplying the result by $16/15$.

Acceptable negative peaks are limited to those which start after the forward systolic peak and within 300 ms of it. The first acceptable negative peak found is marked on the frozen sonogram.

As nearby venous (reverse flow) is often an interfering signal when observing arterial flow, the requirement for real arterial reverse flow to start only after peak systole helps to eliminate such interference. It also helps to prevent wall-thump interference which occurs only at systolic upswing. A first negative peak starting more than 300 ms after the positive peak is not likely to be as a result of local haemodynamic state (may be caused by cardiac regurgitation).

Finally, the waveform is determined to be monotonic if there are no identified positive or negative secondary peaks (notches) and the end diastolic flow is positive. If however at least one forward or reverse notch is detected, the waveform is determined to be non-monotonic. Alternately, if no notches are detected and there is no end diastolic flow, no determination can be made.

The conversion and processing is now complete and the indication of the presence or absence of monotonicity and displayed on the visual display for use by the technician.

If accepted, all relevant data may be stored to disc or other suitable media.

Ensemble Average

Where poor quality, noisy, or low velocity signals are found, the present invention may perform an 'ensemble average' of four screens (16 seconds) of data to produce one clearer, more definite, and statistically relevant waveform for analysis. Once four screens-full of valid data have been obtained, the process of ensemble averaging begins. The longest foot-systolic peak is found amongst all identified cycles. The shortest systolic peak to next foot is similarly found. For each identified systolic peak, a section of sonogram is copied (Systolic peak time−longest foot) to (Systolic peak time+shortest next). These copies are 'superimposed', automatically aligning the data with respect to the systolic peaks (all pixel values summed individually across all identified waveforms then normalized by number summed). This composite waveform is written repeatedly across a 4 second sonogram and displayed. Finally the composite sonogram is subjected to full analysis as though it had been one 4 second sweep, and the results shown.

Supporting Study

In order to establish the accuracy of the present invention in separating significant from non-significant lower limb occlusive disease, a study was conducted, the results of which are described below.

Objectives

Establish the present invention's accuracy in separating significant from non-significant lower limb occlusive disease using Color Duplex as an acceptable modern 'gold standard'.

Examine the distribution of perfusion pressure and 'cuff free ABI' in the significant and non-significant disease groups.

Methods

The study adhered to the provisions of the Declaration of Helsinki. It involved 225 limbs of patients who presented to the vascular lab with symptoms consistent with peripheral artery disease. There were no exclusion criteria. Patient mix included diabetics, claudicants and ischaemic limbs. Symptoms included rest pain, swelling legs and ulcerated extremities. Patients were first tested for significant or non-significant occlusive arterial disease with the present invention. This involves taking an arm BP and acquiring Doppler spectra from the posterior or anterior tibial artery. The present invention automatically identifies the presence of the 'notch' feature which characterizes limbs with none or non-significant arterial disease. A real time statistical analysis rejects 'non physiological' waveforms, then automatically calculates 'cuff free ABI', pedal perfusion pressure and vascular reserve when a minimum of two successive 'valid' waveforms are identified. The patient was then immediately assessed by Color Duplex. Significant occlusive arterial disease criteria ranged from complete occlusion down to and including 50% stenosis (as indicated by a peak systolic velocity ratio of 4 or greater Results Of the 225 limbs evaluated, 119 of them were determined to not have significant disease and 106 were determined to have significant disease.

There were 205 limbs that had a diagnosis that was consistent with the duplex control [true positive]. Three of the patients who were exercised had a false diagnosis that became true after exercise. All three were confirmed by duplex. About 3.1% of the limbs gave an equivocal result and 1.3% of the limbs had an unreadable waveform.

This shows the present invention has a sensitivity of 95.1%, a specificity of 98.2%, and an accuracy of 96.8%. There is less than a 1% false positive rate and a 2.2% false negative rate assuming Duplex is 100 percent correct. (Table 1)

TABLE 1

Outcomes of 225 limbs evaluated by the present invention. [119 negative assessments and 106 positive assessments according to duplex. Positive assessment is defined as >50% stenosis]

| number of limbs | true positive | true negative | false positive | false negative | equivocal | unreadable waveform |
|---|---|---|---|---|---|---|
| 225 | 98 | 110 | 2 | 5 | 7 | 3 |

TABLE 2

Sensitivity, specificity, and accuracy of the present invention in 225 limbs as compared to plain old ABI and Duplex from the literature.

| | Plain old ABI* | Present Invention |
|---|---|---|
| Sensitivity | 77% | 95.10% |
| Specificity | 74% | 98.20% |
| Accuracy | 76% | 96.80% |

*Data taken from Allen, Oates et al 'Comparison of Lower Limb Arterial Assessments Using Color-Duplex Ultrasound and Ankle/Brachial Pressure Index Measurements', Angiology 1996 47: 225, DOI: 10.1177/000331979604700302

The distribution of 'Cuff free' ABI values vs Duplex demonstrated significant/no significant disease evaluation was analyzed. A simple Gaussian distribution was assumed. The following values were obtained:

None or no significant disease on Duplex scan: ABI mean value=0.894+/−0.076 Significant disease on Duplex scan: ABI mean value=0.614 +/−0.137.

It can be seen that the crossover point for the two groups is approximately at the 1 Standard Deviation level (0.75). This is consistent with the lower theoretical maximum value of 1.0 for the 'cuff free' method.

In the true positive group 53.8% of the patients had a vascular reserve of above 15% and the 46.2% of the patients had a vascular reserve of less than 15%. In the true negative group all of the patients had a vascular reserve of greater than 15%. (Table 3)

TABLE 3

Number of limbs with VR <15% after a true positive and true negative assessment

| Vascular Reserve (%) | True positive | True negative |
|---|---|---|
| >0.15 | 50 (53.8%) | 108 (100%) |
| <0.15 | 43 (46.2%) | 0 (0%) |

Of the patients with a true positive outcome 69.2% had a mean perfusion pressure of greater than 40 mmHg and 30.8% of the patients had a mean perfusion pressure of less than 40 mmHg. In the true negative group 99% of the patients had a mean perfusion pressure of greater than 40 mmHg and only 1% of the patients had a mean perfusion pressure of less than 40 mmHg. (Table 4)

TABLE 4

Number of limbs with mean perfusion pressure <40 mmHg after a true positive and true negative assessment

| mean perfusion pressure | true positive | true negative |
|---|---|---|
| >40 mmHg | 36 (69.2%) | 102 (99%) |
| <40 mmHg | 16 (30.8%) | 1 (1%) |

The results from the supporting study demonstrate that the present invention has a sensitivity of 95.1%, a specificity of 98.2%, and an accuracy of 96.8%. There is less than a 1% false positive rate and a 2.2% false negative rate assuming Duplex is 100 percent correct.

Further advantages of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

Additionally, as those skilled in the art will readily recognize, the individual thresholds, timing metrics, filtering criteria, and other similar values stated above may be adjusted, expanded, or condensed as part of an overall implementation strategy without departing form the scope of the present invention.

The invention claimed is:

1. A system comprising:

a transceiver for capturing a representation of blood flow through a blood vessel of interest;

a waveform converter and processor operationally coupled with the transceiver, the waveform converter and processor configured to analyze the representation; and a display operationally coupled to the waveform converter and processor for providing at least one visual indicia for a user;

wherein the waveform converter and processor is configured to detect the presence or absence of any secondary peaks in the representation between a forward systolic peak and end diastole for at least one cardiac cycle; and wherein the waveform converter and processor is configured to filter the detection of any secondary peaks to those which have an amplitude between 5% and 70% of the amplitude of a systolic peak of the cardiac cycle.

2. The system of claim 1, wherein the waveform converter and processor is configured to filter the detection of any reverse flow secondary peaks to those greater than 2/64th of a maximum reverse flow peak.

3. The system of claim 1, wherein the waveform converter and processor is configured to filter the detection of any reverse flow secondary peaks to those greater than 1/128th of a maximum reverse flow peak, greater than a fraction of the maximum reverse flow peak ranging between 1/28th and 1/16th inclusive, or greater than a fraction of the maximum reverse flow peak ranging between 1/64th and 1/8th inclusive.

4. The system of claim 1, wherein the waveform converter and processor is configured to generate a monotonicity indicator if there are no identified secondary peaks or reverse flow secondary peaks and a diastolic flow at the end of the cardiac cycle is positive.

5. The system of claim 1, wherein the waveform converter and processor is configured to reject data from a cardiac cycle if peak to peak time is less than 400 milliseconds or less than 600 milliseconds.

6. The system of claim 1, wherein the waveform converter and processor is configured to regard a negative peak as acceptable if it starts after the forward systolic peak and less than 300 milliseconds after the start of the cardiac cycle, less than 400 milliseconds after the start of the cardiac cycle, or less than 500 milliseconds after the start of the cardiac cycle.

7. The system of claim 1, wherein the transceiver is a Doppler transceiver, and the representation is an audio representation.

8. The system of claim 7, wherein the waveform converter and processor is configured to produce a directional sonogram from the audio representation.

9. The system of claim 8, wherein the waveform converter and processor is configured to generate a maximum frequency outline for both forward and reverse blood flow.

* * * * *